US008688218B2

(12) United States Patent
Pianca

(10) Patent No.: US 8,688,218 B2

(45) Date of Patent: *Apr. 1, 2014

(54) LEAD CONNECTOR FOR AN IMPLANTABLE ELECTRIC STIMULATION SYSTEM AND METHODS OF MAKING AND USING

(75) Inventor: Anne M. Pianca, Santa Monica, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 188 days.

This patent is subject to a terminal disclaimer.

(21) Appl. No.: 13/281,257

(22) Filed: Oct. 25, 2011

(65) Prior Publication Data

US 2012/0041497 A1 Feb. 16, 2012

Related U.S. Application Data

(63) Continuation of application No. 12/104,209, filed on Apr. 16, 2008, now Pat. No. 8,046,073.

(51) Int. Cl.
*A61N 1/372* (2006.01)

(52) U.S. Cl.
USPC .......... 607/37

(58) Field of Classification Search
USPC .......... 607/117, 122–123
See application file for complete search history.

(56) References Cited

U.S. PATENT DOCUMENTS

| | | | |
|---|---|---|---|
| 5,843,141 | A | 12/1998 | Bischoff et al. |
| 6,181,969 | B1 | 1/2001 | Gord |
| 6,321,126 | B1 | 11/2001 | Kuzma |
| 6,370,434 | B1 | 4/2002 | Zhang et al. |
| 6,516,227 | B1 | 2/2003 | Meadows et al. |
| 6,609,029 | B1 | 8/2003 | Mann et al. |
| 6,609,032 | B1 | 8/2003 | Woods et al. |
| 6,671,534 | B2 | 12/2003 | Putz |
| 6,741,892 | B1 | 5/2004 | Meadows et al. |
| 7,244,150 | B1 | 7/2007 | Brase et al. |
| 7,437,193 | B2 | 10/2008 | Parramon |
| 7,672,734 | B2 | 3/2010 | Anderson |
| 7,761,165 | B1 | 7/2010 | He et al. |
| 7,949,395 | B2 | 5/2011 | Kuzma |
| 7,974,706 | B2 | 7/2011 | Moffitt |
| 8,046,073 | B1 | 10/2011 | Pianca |
| 2005/0165465 | A1 | 7/2005 | Pianca |
| 2007/0150036 | A1 | 6/2007 | Anderson |
| 2007/0219595 | A1 | 9/2007 | He |
| 2008/0071320 | A1 | 3/2008 | Brase |

OTHER PUBLICATIONS

Official Communication for U.S. Appl. No. 12/104,209 mailed Aug. 4, 2011.

*Primary Examiner* — Luther Behringer

(74) *Attorney, Agent, or Firm* — Frommer Lawrence & Haug LLP; Patrick R. Turner

(57) ABSTRACT

A lead-connection system includes a lead and a connector. The lead includes a distal end, a proximal end, a plurality of electrodes disposed at the distal end, a plurality of terminals disposed at the proximal end, and a plurality of conductor wires electrically coupling each of the plurality of electrodes to a different one of the plurality of terminals. The connector defines a port for receiving the proximal end of the lead and a plurality of connector contacts. The number of connector contacts is greater than the number of terminals disposed on the proximal end of the lead. When the connector receives the proximal end of the lead, each of the terminals disposed on the proximal end of the lead makes electrical contact with at least one of the connector contacts of the connector and no two terminals make electrical contact with a same one of the connector contacts.

20 Claims, 10 Drawing Sheets

404 402 406 440 606 424 428 414 602 432 422 434 608 415 604 416 417 426 410 430 418 419 420 421

LEAD CONNECTOR FOR AN IMPLANTABLE ELECTRIC STIMULATION SYSTEM AND METHODS OF MAKING AND USING

CROSS-REFERENCE TO RELATED APPLICATIONS

This patent application is a continuation of U.S. patent application Ser. No. 12/104,209 filed on Apr. 16, 2008, now U.S. Pat. No. 8,046,073 issued on Oct. 25, 2011, which is incorporated herein by reference.

TECHNICAL FIELD

The present invention is directed to the area of implantable electrical stimulation systems and methods of making and using the systems. The present invention is also directed to implantable electrical stimulation systems that include a connector that includes connector contacts configured and arranged to couple electrically with leads having different numbers of terminals arranged in different orientations, as well as methods of making and using the connectors and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Deep brain stimulation has also been useful for treating refractory chronic pain syndromes and has been applied to treat movement disorders and epilepsy. Peripheral nerve stimulation has been used to treat chronic pain syndrome and incontinence, with a number of other applications under investigation. Functional electrical stimulation systems have been applied to restore some functionality to paralyzed extremities in spinal cord injury patients. Moreover, electrical stimulation systems can be implanted subcutaneously to stimulate subcutaneous tissue including subcutaneous nerves such as the occipital nerve.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

In one embodiment, a lead-connection system includes a lead with a distal end and a proximal end. The lead includes a plurality of electrodes disposed at the distal end, a plurality of terminals disposed at the proximal end, and a plurality of conductor wires disposed along the lead to electrically couple each of the plurality of electrodes to a different one of the plurality of terminals. The lead-connection system also includes a connector configured and arranged for receiving the proximal end of the lead. The connector defines a port configured and arranged for receiving the proximal end of the lead. The connector also includes a plurality of connector contacts disposed in the connector. The number of connector contacts is greater than the number of terminals disposed on the proximal end of the lead. When the connector receives the proximal end of the lead, each of the plurality of terminals disposed on the proximal end of the lead makes electrical contact with at least one of the connector contacts of the connector and no two terminals make electrical contact with a same one of the connector contacts.

In another embodiment, an electrical stimulating system includes a lead having a distal end and a proximal end. The lead includes a plurality of electrodes disposed at the distal end, a plurality of terminals disposed at the proximal end, and a plurality of conductor wires coupling the plurality of electrodes electrically to the plurality of terminals. The electrical stimulating system also includes a control module configured and arranged to electrically couple to the lead. The control module includes a housing and an electronic subassembly disposed in the housing. The electrical stimulating system also includes a connector configured and arranged for receiving the proximal end of the lead. The connector defines a port configured and arranged for receiving the proximal end of the lead. The connector also includes a plurality of connector contacts disposed in the connector. The number of connector contacts is greater than the number of terminals disposed on the proximal end of the lead. When the connector receives the proximal end of the lead, each of the plurality of terminal disposed on the proximal end of the lead makes electrical contact with at least one of the connector contacts of the connector and no two terminals make electrical contact with a same one of the connector contacts.

In yet another embodiment, a method of implanting a lead into a patient and disposing the proximal end of the lead into a connector. The lead includes a plurality of electrodes at a distal end of the lead. The electrodes are electrically coupled to a plurality of terminals disposed on a proximal end of the lead by a plurality of contact wires. The connector defines at least one port for receiving the proximal end of the lead. The at least one port includes a plurality of connective contacts that electrically couple to at least one of the plurality of terminals where the number of connector contacts is greater than the number of terminals disposed on the proximal end of the lead and no two terminals make electrical contact with a same one of the connector contacts. The method further includes providing electrical signals from the at least one control module to electrically stimulate patient tissue using at least one of the plurality of electrodes disposed on the lead.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed to implantable electrical stimulation systems that include a connector that includes connector contacts configured and arranged to couple electrically with leads having different numbers of terminals arranged in different orientations, as well as methods of making and using the connectors and electrical stimulation systems.

Suitable implantable electrical stimulation systems include, but are not limited to, an electrode lead ("lead") with one or more electrodes disposed on a distal end of the lead and one or more terminals disposed on one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; and 6,741,892; and U.S. patent application Ser. Nos. 10/353,101, 10/503,281, 11/238,240; 11/319,291; 11/327,880; 11/375,638; 11/393,991; and 11/396,309, all of which are incorporated by reference.

Figure 1:
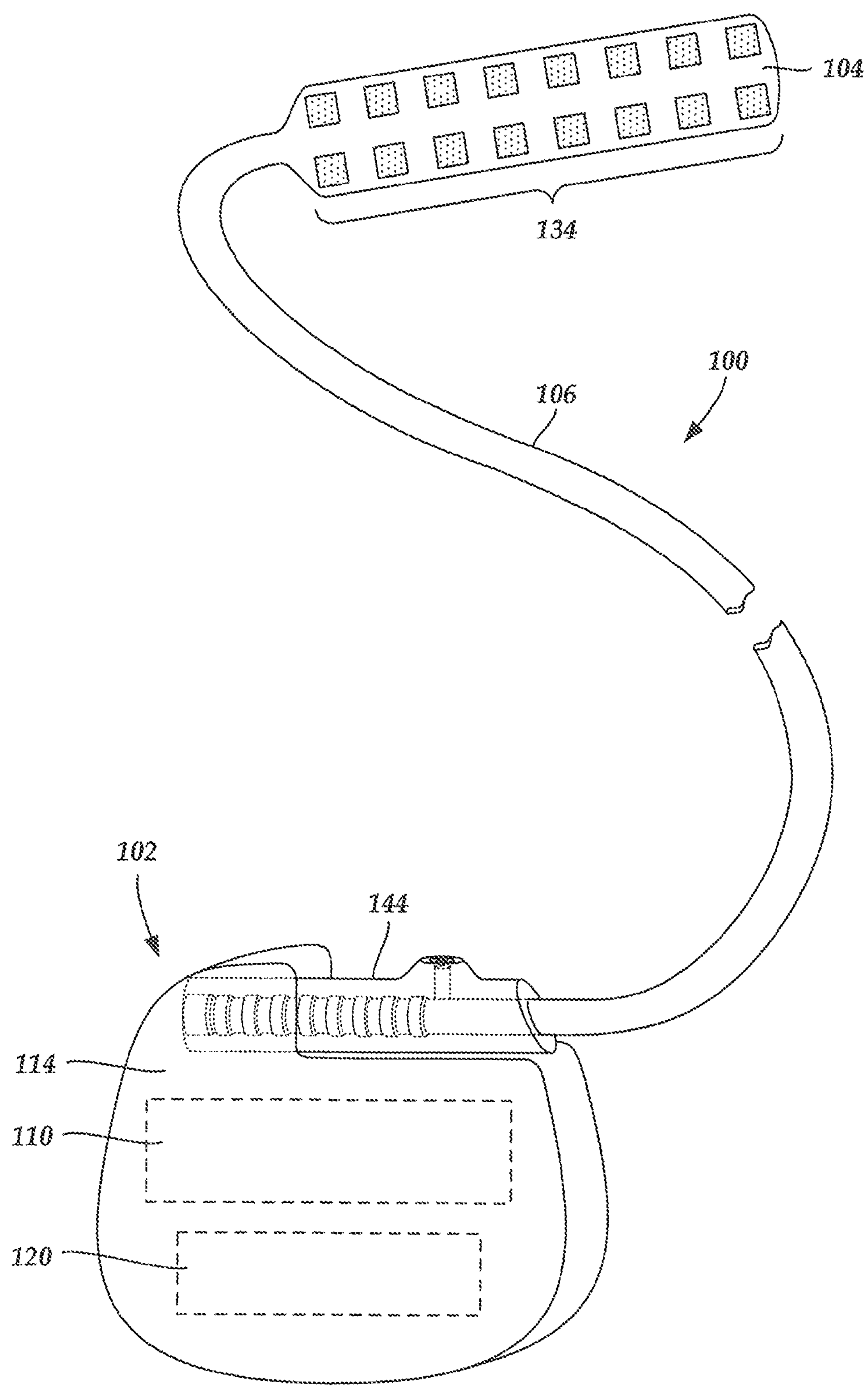
FIG. 1 is a schematic view of one embodiment of an electrical stimulation system, according to the invention.
Figure 2:
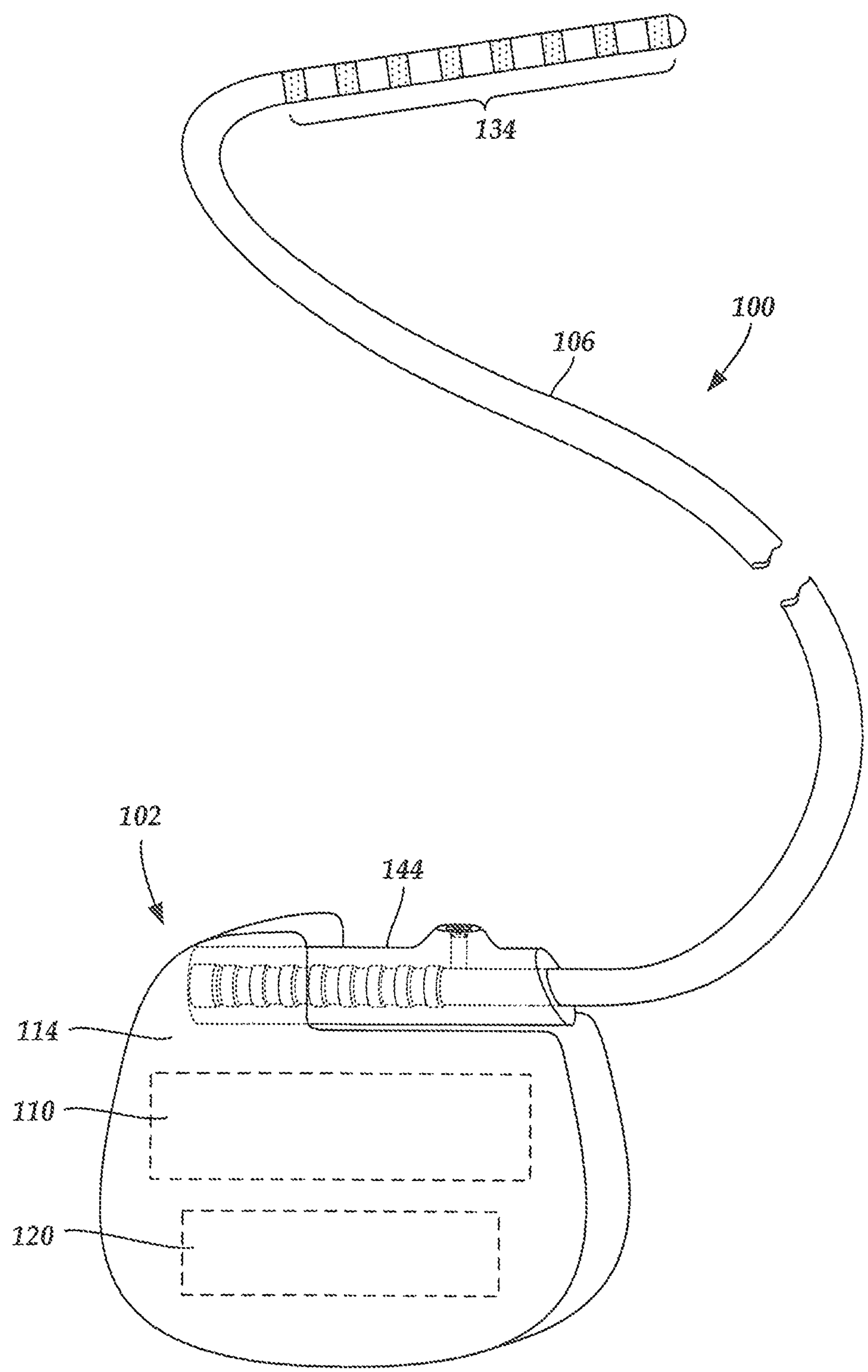
FIG. 2 is a schematic view of another embodiment of an electrical stimulation system, according to the invention.

FIG. 1 illustrates schematically one embodiment of an electrical stimulation system 100. The electrical stimulation system includes a control module (e.g., a stimulator or pulse generator) 102, a paddle body 104, and at least one lead body 106 coupling the control module 102 to the paddle body 104. The paddle body 104 and the one or more lead bodies 106 form a lead. The paddle body 104 typically includes an array of electrodes 134. The control module 102 typically includes an electronic subassembly 110 and an optional power source 120 disposed in a sealed housing 114. The control module 102 typically includes a connector 144 (FIGS. 2 and 3A, see also 322 and 350 of FIG. 3B) into which the proximal end of the one or more lead bodies 106 can be plugged to make an electrical connection via connector contacts on the control module 102 and terminals (e.g., 310 in FIG. 3A and 336 of FIG. 3B) on each of the one or more lead bodies 106. It will be understood that the electrical stimulation system can include more, fewer, or different components and can have a variety of different configurations including those configurations disclosed in the electrical stimulation system references cited herein. For example, instead of a paddle body 104, the electrodes 134 can be disposed in an array at or near the distal end of the lead body 106 forming a percutaneous lead, as illustrated in FIG. 2. A percutaneous lead may be isodiametric along the length of the lead. In addition, one or more lead extensions 324 (e.g., FIG. 3B) can be disposed between the one or more lead bodies 106 and the control module 102 to extend the distance between the one or more lead bodies 106 and the control module 102 of the embodiments shown in FIGS. 1 and 2.

The electrical stimulation system or components of the electrical stimulation system, including one or more of the lead bodies 106, the paddle body 104, and the control module 102, are typically implanted into the body of a patient. The electrical stimulation system can be used for a variety of applications including, but not limited to, brain stimulation, neural stimulation, spinal cord stimulation, muscle stimulation, and the like.

The electrodes 134 can be formed using any conductive, biocompatible material. Examples of suitable materials include metals (e.g., platinum or titanium), alloys (e.g., platinum/iridium), conductive polymers, conductive carbon, and the like, as well as combinations thereof. The number of electrodes 134 in the array of electrodes 134 may vary. For example, there can be two, four, six, eight, ten, twelve, fourteen, sixteen, or more electrodes 134. As will be recognized, other numbers of electrodes 134 may also be used.

The electrodes of the paddle body 104 or one or more lead bodies 106 are typically disposed in, or separated by, a non-conductive, biocompatible material such as, for example, silicone, polyurethane, polyetheretherketone ("PEEK"), epoxy, and the like or combinations thereof. The paddle body 104 and one or more lead bodies 106 may be formed in the desired shape by any process including, for example, molding (including injection molding), casting, and the like. Electrodes and connecting wires can be disposed onto or within a paddle body either prior to or subsequent to a molding or casting process. The non-conductive material typically extends from the distal end of the lead to the proximal end of each of the one or more lead bodies 106. The non-conductive, biocompatible material of the paddle body 104 and the one or more lead bodies 106 may be the same or different. The paddle body 104 and the one or more lead bodies 106 may be a unitary structure or can be formed as two separate structures that are permanently or detachably coupled together.

Terminals (e.g., 310 in FIG. 3A and 336 of FIG. 3B) are typically disposed at the proximal end of the one or more lead bodies 106 for connection to corresponding connector contacts (e.g., 314 in FIG. 3A and 340 of FIG. 3B) in connectors (e.g., 144 in FIGS. 1-3A and 322 and 350 of FIG. 3B) disposed on, for example, the control module 102 (or to other devices, such as connector contacts on a lead extension, an operating room cable, or an adaptor). Conductor wires (not shown) extend from the terminals (e.g., 310 in FIG. 3A and 336 of FIG. 3B) to the electrodes 134. Typically, one or more electrodes 134 are electrically coupled to a terminal (e.g., 310 in FIG. 3A and 336 of FIG. 3B). In some embodiments, each terminal (e.g., 310 in FIG. 3A and 336 of FIG. 3B) is only connected to one electrode 134. The conductor wires may be embedded in the non-conductive material of the lead or can be disposed in one or more lumens (not shown) extending along the lead. In some embodiments, there is an individual lumen for each conductor wire. In other embodiments, two or more conductor wires may extend through a lumen. There may also be one or more lumens (not shown) that open at, or near, the proximal end of the lead, for example, for inserting a stylet rod to facilitate placement of the lead within a body of a patient. Additionally, there may also be one or more lumens (not shown) that open at, or near, the distal end of the lead, for example, for infusion of drugs or medication into the site of implantation of the paddle body 104. In at least one embodiment, the one or more lumens may be flushed continually, or on a regular basis, with saline, epidural fluid, or the like. In at least some embodiments, the one or more lumens can be permanently or removably sealable at the distal end.

Figure 3A:
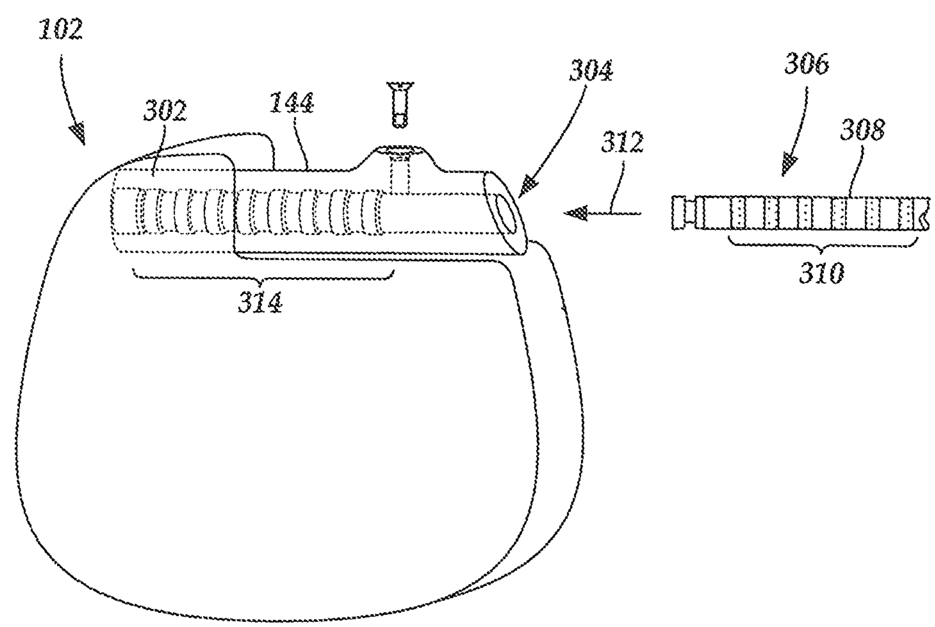
FIG. 3A is a schematic view of one embodiment of a proximal portion of a lead and a control module of an electrical stimulation system, according to the invention.

In at least some embodiments, leads are coupled with connectors disposed as part of a control module. In at least some embodiments, leads are coupled with connectors disposed on lead extensions. In other embodiments, leads are coupled with connectors disposed on other devices, such as an operating room cable or an adaptor. In at least some embodiments, fastening assemblies can be used to secure a coupling of a lead with a connector. In FIG. 3A, the connector 144 is shown disposed on the control module 102. The connector 144 includes a connector housing 302. The connector housing 302 defines at least one port 304 into which a proximal end 306 of a lead 308 with terminals 310 can be inserted, as shown by directional arrow 312. The connector housing 302 also includes a plurality of connector contacts 314 for each port 304. When the lead 308 is inserted into the port 304, the connector contacts 314 can be aligned with the terminals 310 on the lead 308 to electrically couple the control module 102 to the electrodes (134 of FIG. 1) disposed at a distal end of the lead 308. Examples of connectors in control modules are found in, for example, U.S. Pat. No. 7,244,150 and U.S. patent application Ser. No. 11/532,844, which are incorporated by reference.

Figure 3B:
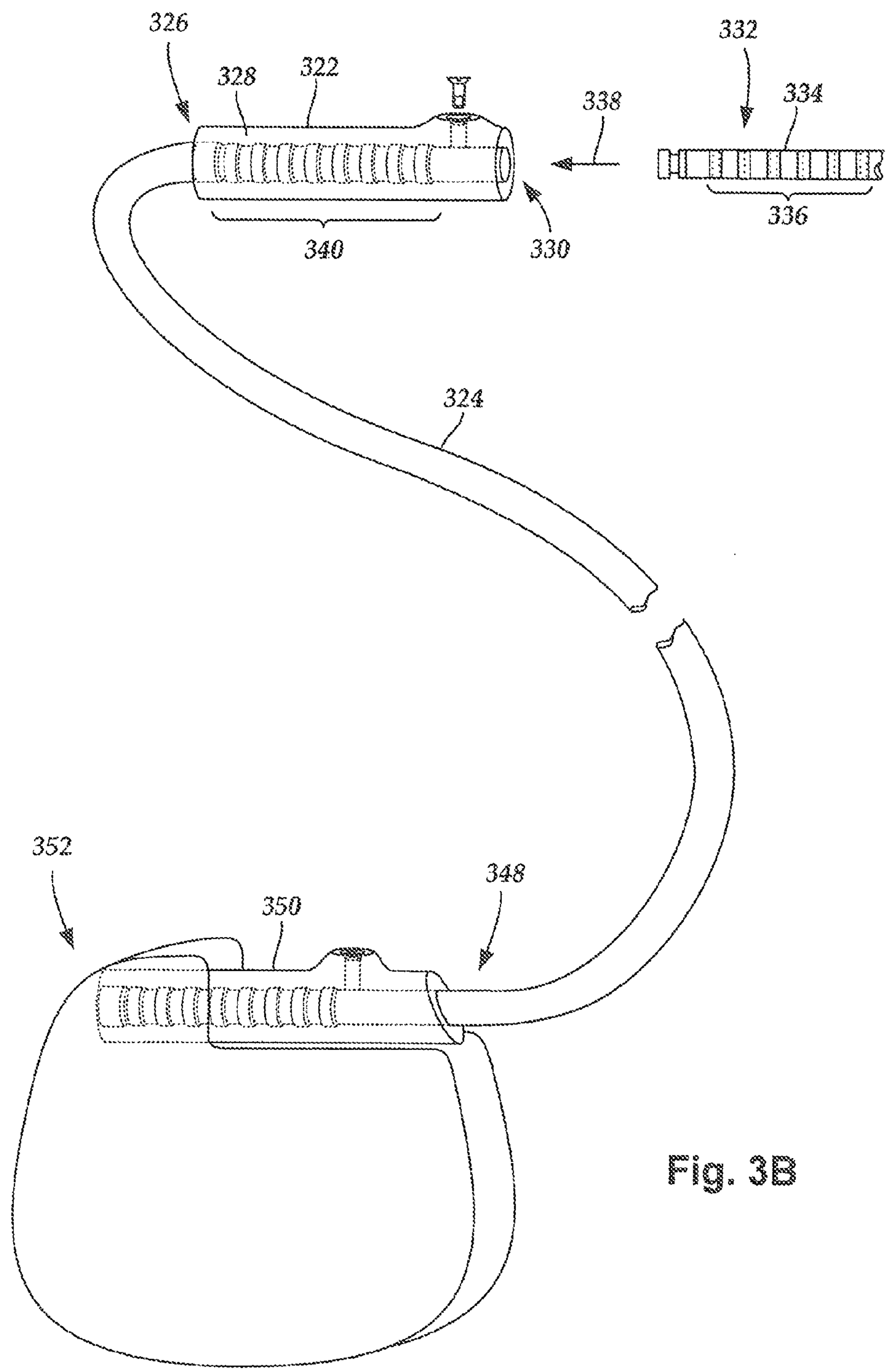
FIG. 3B is a schematic view of one embodiment of a proximal portion of a lead and a lead extension of an electrical stimulation system, according to the invention.

In FIG. 3B, a connector 322 is disposed on a lead extension 324. The connector 322 is shown disposed at a distal end 326 of the lead extension 324. The connector 322 includes a connector housing 328. The connector housing 328 defines at least one port 330 into which a proximal end 332 of a lead 334 with terminals 336 can be inserted, as shown by directional arrow 338. The connector housing 328 also includes a plurality of connector contacts 340. When the lead 334 is inserted into the port 330, the connector contacts 340 disposed in the connector housing 328 can be aligned with the terminals 336 on the lead 334 to electrically couple the lead extension 324 to the electrodes (134 of FIG. 1) disposed at a distal end (not shown) of the lead 334.

In at least some embodiments, the proximal end of a lead extension is similarly configured and arranged to a proximal end of a lead. The lead extension 324 may include a plurality of conductive wires (not shown) that electrically couple the connector contacts 340 to a proximal end 348 of the lead extension 324 that is opposite to the distal end 326. In at least some embodiments, the conductive wires disposed in the lead extension 324 can be electrically coupled to a plurality of terminals (not shown) disposed on the proximal end 348 of the lead extension 324. In at least some embodiments, the proximal end 348 of the lead extension 324 is configured and arranged for insertion into a connector disposed in another lead extension. In other embodiments, the proximal end 348 of the lead extension 324 is configured and arranged for insertion into a connector disposed in a control module. For example, in FIG. 3B the proximal end 348 of the lead extension 324 is inserted into a connector 350 disposed in a control module 352. Note that, when a lead includes two or more proximal ends, each proximal end can be inserted into one of a plurality of ports defined in a connector, with each port including a plurality of connector contacts.

Advancements in technology may create changes in electrical stimulation systems over time. Patients undergoing multiple implantations/explantations over an extended period of time may receive one or more new devices that are not readily compatible with currently-implanted devices. For example, a patient with a malfunctioning currently-implanted control module may need to undergo a subsequent surgical procedure to replace the malfunctioning control module. However, the malfunctioning control module may be designed to couple to an eight-terminal lead and the replacement control module may be designed to couple to a sixteen-terminal lead. Thus, the currently-implanted lead may not be readily compatible with the replacement control module. In some cases, an adapter may be used to couple two otherwise incompatible devices. However, conceiving, testing, and implanting an adapter may add time to a surgical procedure and add another potential source of device error or human error.

Figure 4:
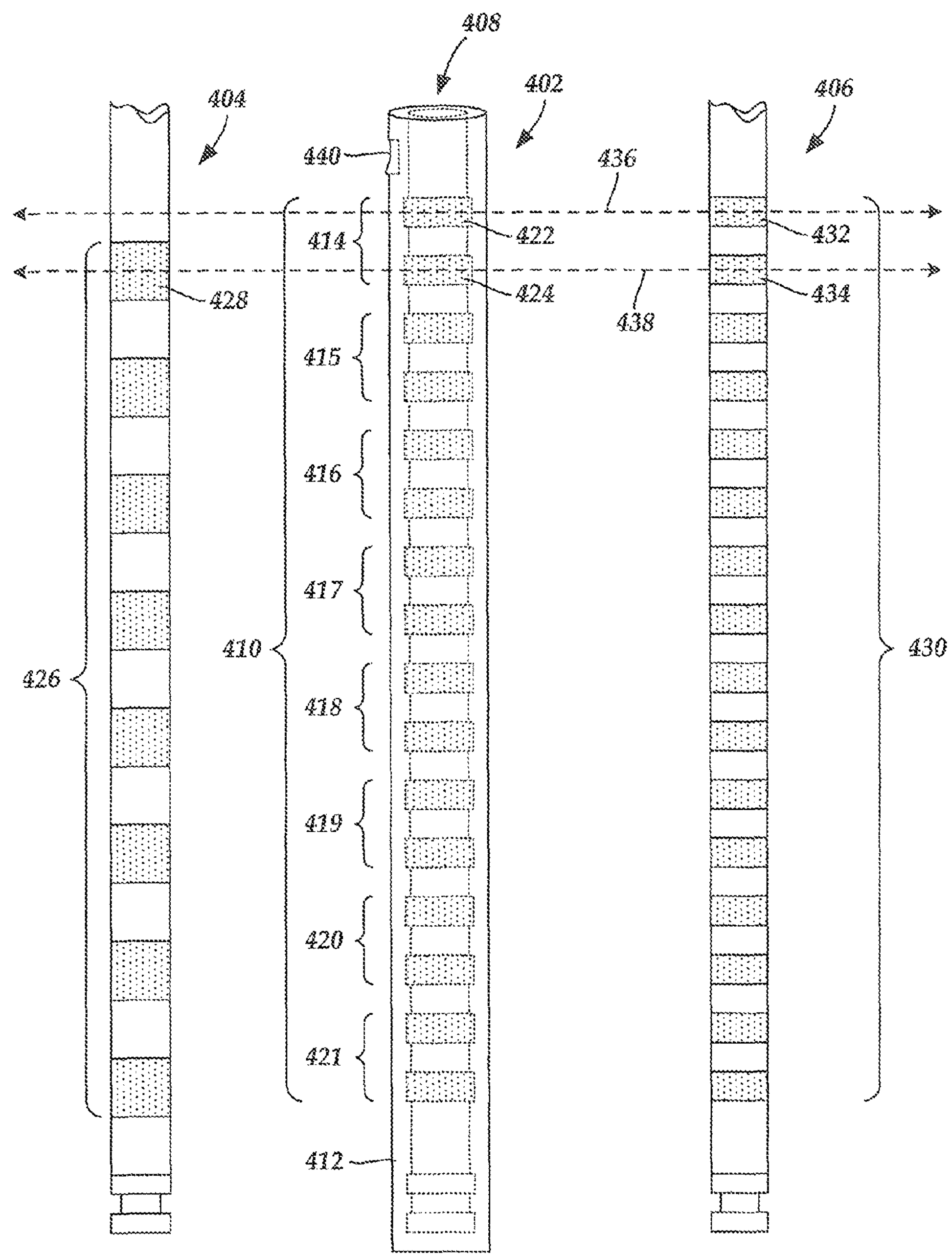
FIG. 4 is a schematic side view of one embodiment of a connector positioned between a portion of a proximal end of an eight-terminal lead and a portion of a proximal end of a sixteen-terminal lead, the connector having connector contacts disposed in the connector that align with terminals disposed on either the eight-terminal lead or the sixteen-terminal lead when either the eight-terminal lead or the sixteen-terminal lead is inserted into the connector, according to the invention.

In at least some embodiments, a lead-connection system includes a connector that is compatible with leads having different numbers of terminals, leads having different terminal orientations, or leads having different proximal-end cross-sectional shapes. Leads may include many different numbers of terminals. For example, a lead may have one, two, three, four, eight, sixteen, thirty-two, sixty-four, or more terminals. It will be understood that leads can also have other numbers of terminals. In FIG. 4, and in subsequent figures, eight-terminal leads and sixteen-terminal leads are used as examples showing the compatibility of the connector for electrically coupling leads with different numbers of terminals. However, in at least some embodiments, the connector can also electrically couple leads with more or less than eight or sixteen terminals. Note that it may be advantageous to have a proximal end of a lead with terminal sizes, terminal spacing, and a cross-sectional shape that differs from the electrode sizes, electrode spacing, and the cross-sectional shape of the distal end of the lead in order distinguish leads with different distal ends for different specific applications.

In some embodiments, when a sixteen-terminal lead is inserted into a connector, each connector contact disposed on the connector aligns (and electrically couples) with each terminal disposed on the lead. However, when an eight-terminal lead is inserted into that same connector, every other connector contact disposed in the connector aligns (and electrically couples) with a terminal disposed on the lead. In at least some embodiments, when a proximal end of a lead with terminals is inserted into a connector with connector contacts and one or more of the terminals align with one or more of the connector contacts, the aligned connector contact(s) and terminals) also couple electrically to one another.

Figure 5:
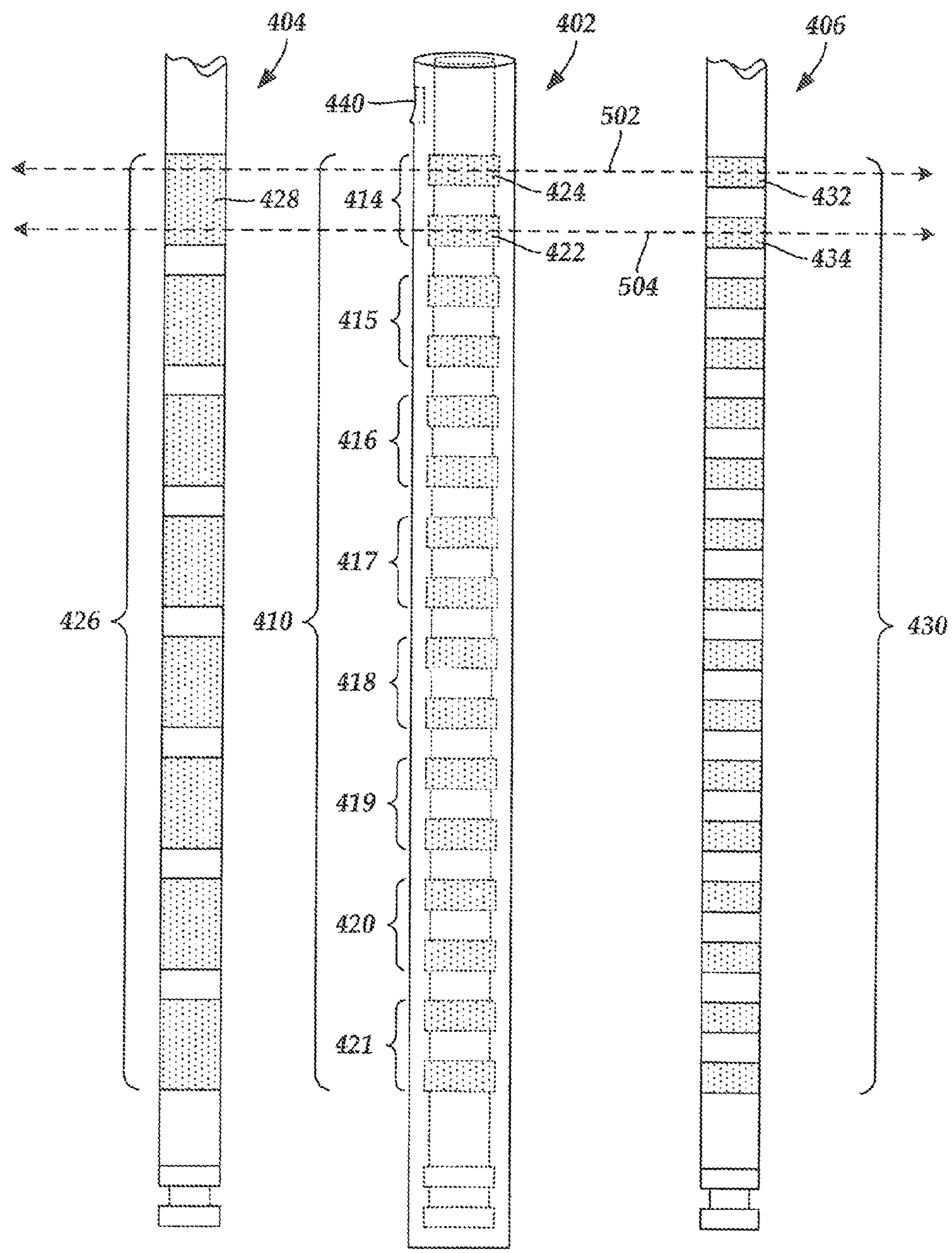
FIG. 5 is a schematic side view of a second embodiment of a connector positioned between a portion of a proximal end of an eight-terminal lead and a portion of a proximal end of a sixteen-terminal lead, the connector having connector contacts disposed in the connector that align with terminals disposed on either the eight-terminal lead or the sixteen-terminal lead when either the eight-terminal lead or the sixteen-terminal lead is inserted into the connector, according to the invention.
Figure 6:
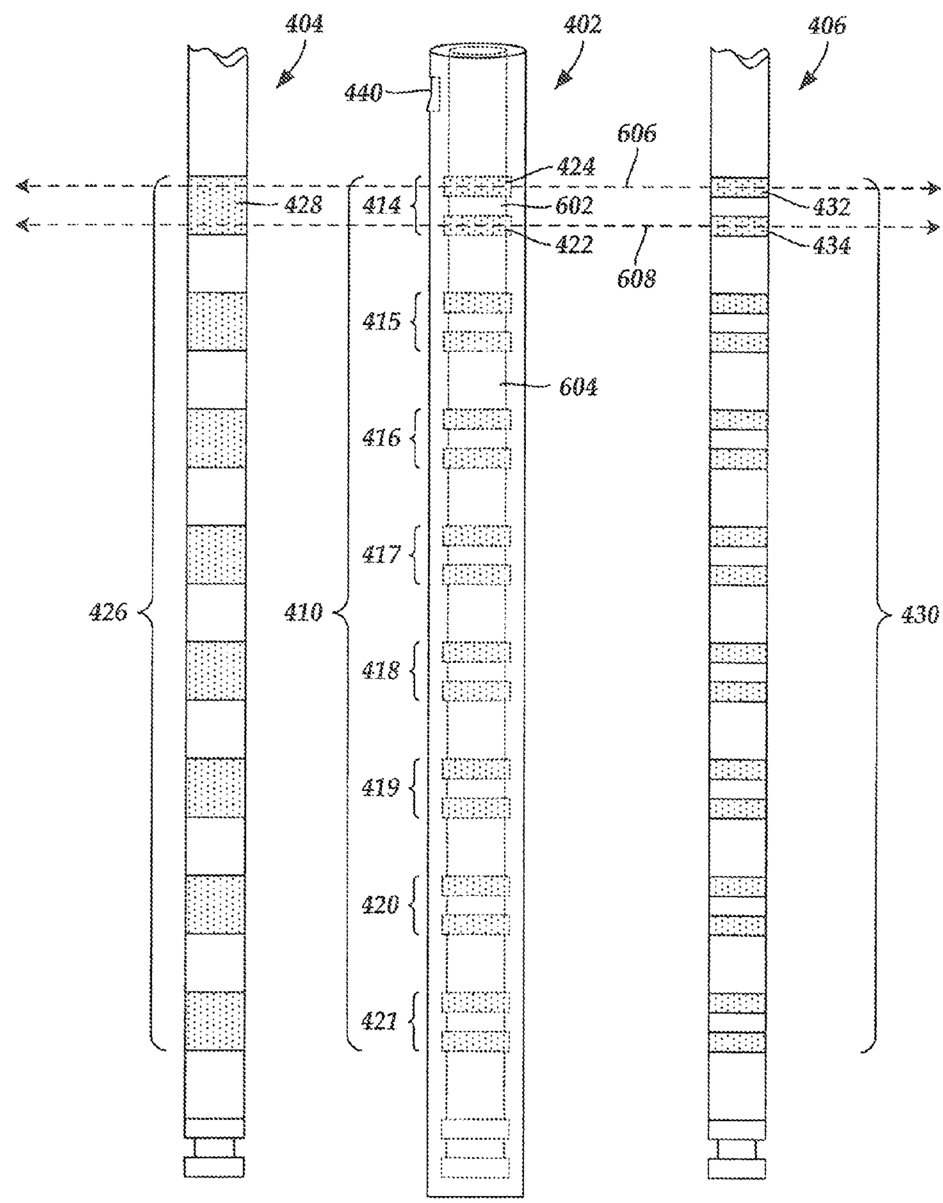
FIG. 6 is a schematic side view of a third embodiment of a connector positioned between a portion of a proximal end of an eight-terminal lead and a portion of a proximal end of a sixteen-terminal lead, the connector having connector contacts disposed in the connector that align with terminals disposed on either the eight-terminal lead or the sixteen-terminal lead when either the eight-terminal lead or the sixteen-terminal lead is inserted into the connector, according to the invention.

FIGS. 4-6 each show a different embodiment of a connector positioned between two different leads for illustrative purposes. Each connector embodiment is configured and arranged to receive a single lead that can be selected from either of the leads shown with each connector embodiment. FIG. 4 is a schematic side view of one embodiment of a connector 402 positioned between a portion of a proximal end of an eight-terminal lead 404 and a portion of a proximal end of a sixteen-terminal lead 406. The connector 402 includes a port 408 and connector contacts 410 disposed in a connector housing 412. The connector contacts 410 can be grouped into sets 414-421 of adjacent connector contacts 410. In FIG. 4, and in subsequent figures, sets are shown as including two connector contacts for clarity of illustration. Sets can include many different numbers of connector contacts. For example, sets can include two, three, four, five, six, seven, eight, nine, ten, or more connector contacts in a set. It will be understood that sets may also include other numbers of connector contacts. In FIG. 4, each set 414-421 of connector contacts 410 includes a first connector contact, such as first connector contact 424, and a second connector contact, such as second connector contact 422. In at least some embodiments, the designation of the first connector contacts and the second connector contacts in each set 414-421 of connector contacts 410 is based solely on the relative positioning of the first connector contacts and the second connector contacts within each set 414-421 of connector contacts 410.

The eight-terminal lead 404 includes a plurality of terminals 426, such as terminal 428, and the sixteen-terminal lead 406 includes a plurality of terminals 430, such as terminals 432 and 434. Each of the connector contacts 410 in the connector 402 is configured and arranged to align (and electrically couple) with one of the plurality of terminals 430 disposed on the sixteen-terminal lead 406 when the sixteen-terminal lead 406 is inserted into the port 408. For example, in FIG. 4, the first connector contact 424 and the second connector contact 422 are as shown aligned with the terminals 434 and 432, respectively, of the sixteen-terminal lead 406, as shown by two-headed dashed arrows 438 and 436, respectively. Thus, in at least some embodiments, when the sixteen-terminal lead 406 is inserted into the port 408, each connector contact 410 aligns (and electrically couples) to one of the terminals 430.

However, only one connector contact of each set. 414-421 of connector contacts 410 is configured and arranged to align (and electrically couple) with each of the plurality of terminals 426 disposed on the eight-terminal lead 404 when the eight-terminal lead 404 is inserted into the port 408. For example, in FIG. 4, the first connector contact 424 aligns with the terminal 428 of the eight-terminal lead 404, as shown by the two-headed arrow 438. However, the second connector contact 422 does not align with any terminals of the eight-terminal lead 404, as shown by the two-headed arrow 436. Thus, in at least some embodiments, when the eight-terminal lead 404 is inserted into the port 408, each of the first connector contacts aligns (and electrically couples) to one of the terminals 426 and none of the second connector contacts aligns (and electrically couples) with any of the terminals 426.

In at least some embodiments, the connector 402 may include a switch, such as switch 440, for controlling the functioning of one or more of the connector contacts. In some embodiments, the switch 440 may be used to de-activate unused connector contacts. For example, the switch 440 may have a first position and a second position. The first position may correspond to the activation of each of the connector contacts 410 and the second position may correspond to the de-activation of the second connector contacts. Thus, the switch 440 may be placed in the first position when the sixteen-terminal lead 406 is inserted into the port 408, and placed in the second position when the eight-terminal lead 404 is inserted into the port 408. De-activation of unused connector contacts may provide an advantage by avoiding energy waste, current leakage, and pocket stimulation within the connector 402. In some embodiments, the switch 440 is disposed on the connector 402. In other embodiments, the switch 440 is disposed on the control module (102 in FIGS. 1-3A and 352 in FIG. 3B) or is implemented through software in the control module as described below.

In alternate embodiments, the switch 440 may have additional positions that may de-activate different connector contacts. For example, another position may de-activate the first connector contacts, another position may de-activate the eight most distal connector contacts, another position may de-activate the eight most proximal connector contacts, another position may de-activate one or more sets of connector contacts, and another position may de-activate the first three connector contacts of every set of connector contacts. It will be understood that many other conductive-contact-deactivation combinations are possible. In an alternate embodiment, a separate on/off switch may control each individual connector contact to customize the orientation of connector contact activation. Many different types of switches may be used. For example, switches may include mechanical switches, electrical switches, and the like or combinations thereof.

Additionally or alternatively, a switch or switches can also be implemented in software. For example, the connector 402 (or a lead to be input to the connector 402) may include a feature that activates the switch instead of having a healthcare professional manually activated during implantation of an electrical stimulation system. In some embodiments, the switch is activated by one or more electronic sensors disposed in the connector 402 (or a lead to be input to the connector 402) or by testing properties of the lead or connector contacts (e.g., the resistance of a connector contact, which will generally be higher if a terminal is not aligned with the connector contact). In other embodiments, a software switch is activated by a healthcare professional or another by inputting a signal into a user interface of an electronic device in electrical communication with the control module or another component of the electrical stimulation system.

As shown in FIG. 4, the sizes of the connector contacts 410 disposed in the connector 402 are narrower and more closely-spaced than the terminals 426 disposed on the eight-terminal lead 404. However, the connector contacts 410 disposed in the connector 402 are approximately equal in size and spacing to the terminals 430 disposed on the sixteen-terminal lead 406. In some embodiments, the sizing and spacing of either or both the connector contacts 410 of the connector 402 and the terminals 430 of the sixteen-terminal lead 406 can be modified to align with one another, and collectively modified so that the first connector contact of each set 414-421 of connector contacts 410 aligns with one of the terminals 426 of the eight-terminal lead 404.

In some embodiments, when a sixteen-terminal lead is inserted into a connector, each connector contact disposed on the connector aligns (and electrically couples) with a terminal disposed on the sixteen-terminal lead. However, when an eight-terminal lead is inserted into the connector, each connector contact within a set of connector contacts align (and electrically couple) with a terminal disposed on the eight-terminal lead. In at least some embodiments, when either an eight-terminal lead or a sixteen-terminal lead is inserted into a connector, one or more connector contacts align (and electrically couple) with each terminal. However, no more than one terminal aligns (and electrically couples) with each connector contact.

FIG. 5 is a schematic side view of a second embodiment of the connector 402 positioned between a portion of a proximal end of the eight-terminal lead 404 and a portion of a proximal end of the sixteen-terminal lead 406. When the sixteen-terminal lead 406 is inserted into the connector 402, each of the connector contacts 410 disposed on the connector 402 aligns (and electrically couples) with one of the terminals 430 disposed on the sixteen-terminal lead 406. For example, in FIG. 5, the first connector contact 424 and the second connector contact 422 of the set 414 of connector contacts 410 are shown aligned with the terminals 434 and 432, respectively, of the sixteen-terminal lead 406, as shown by two-headed dashed arrows 504 and 502, respectively.

When the eight-terminal lead 404 is inserted into the connector 402, each connector contact of each set 414-421 of connector contacts 410 align (and electrically couple) with each terminal of the plurality of terminals 426 disposed on the eight-terminal lead 404. For example, in FIG. 5, the first connector contact 424 and the second connector contact 422 are both shown aligned with the terminal 428 of the eight-terminal lead 404, as shown by the two-headed dashed arrows 606 and 608. Thus, in at least some embodiments, each terminal of a lead may align (and electrically couple) with a plurality of connector contacts. The number of connector contacts that may align (and electrically couple) with terminals disposed on an inserted lead may vary, depending on the number of connector contacts in a set of connector contacts.

In some embodiments, a switch may be used to de-activate one or more of a plurality of connector contacts aligning (and electrically coupling) with a given terminal. In at least some embodiments, the switch 440 de-activates all but one of the connector contacts aligning (and electrically coupling) each terminal. For example, the switch 440 can be used to de-activate either the first connector contact 424 or the second connector contact 422 of the set 414 of connector contacts 410, both of which align with the terminal 428. In alternate embodiments, an algorithm may be employed by a coupled processor disposed, for example, in an electrically coupled control module to determine how much current to pass through each of a plurality of connector contacts electrically coupled to an individual terminal disposed on an inserted lead.

In at least some embodiments, the distance between connector contacts within a set of connector contacts may not be equal to the distance between adjacent sets of connector contacts. FIG. 6 is a schematic side view of a third embodiment of a connector 402 positioned between a portion of a proximal end of an eight-terminal lead 404 and a portion of a proximal end of a sixteen-terminal lead 406. The connector 402 includes a plurality of sets 414-421 of connector contacts 410. Each set 414-421 of connector contacts 410 includes a first connector contact, such as the first connector contact 424, and a second connector contact, such as the second connector contact 422. First connector contacts and second connector contacts are separated from one another by an intra-set distance, such as intra-set distance 602 separating the first connector contact 424 from the second connector contact 422. Additionally, the connector contacts within a set 414-421 of connector contacts 410 are separated from one another by an inter-set distance, such as inter-set distance 604 separating the set 415 of connector contacts 410 from the set 416 of connector contacts 410. In at least some embodiments, inter-set distances are greater in length than intra-set distances. For example, as shown in FIG. 6, the inter-set distance 604 is greater in length than the intra-set distance 602. In other embodiments, inter-set distances and intra-set distances are approximately equal in length (as shown in FIGS. 4 and 5). In yet other embodiments, intra-set distances are greater in length than inter-set distances.

As shown in FIG. 6, each of the terminals 430 disposed on the sixteen-terminal lead 406 are configured and arranged to align (and electrically couple) with one of the connector contacts 410 disposed in the connector 404. When the sixteen-terminal lead 406 is inserted into the connector 402, each of the connector contacts 410 disposed on the connector 402 align (and electrically couple) with one of the terminals 430 disposed on the sixteen-terminal lead 406. For example, in FIG. 6, the first connector contact 424 and the second connector contact 422 are shown aligned with the terminals 434 and 432, respectively, of the sixteen-terminal lead 406, as shown by two-headed dashed arrows 608 and 606, respectively.

When the eight-terminal lead 404 is inserted into the connector 402, both the first connector contact and the second connector contact of each set 414-421 of connector contacts 410 align (and electrically couple) with each terminal of the plurality of terminals 426 disposed on the eight-terminal lead 404. For example, in FIG. 6, the first connector contact 424 and the second connector contact 422 are both shown aligned with the terminal 428 of the eight-terminal lead 404, as shown by the two-headed dashed arrows 606 and 608.

In some embodiments, a switch may be used to de-activate one or more of a plurality of connector contacts aligning (and electrically coupling) with a given terminal. For example, the switch 440 can be used to de-activate either the first connector contact 424 or the second connector contact 422 of the set 414, both of which align with the terminal 428. In alternate embodiments, an algorithm may be employed by a coupled processor disposed, for example, in an electrically coupled control module to determine how much current to pass through each of a plurality of connector contacts electrically coupled to an individual terminal disposed on an inserted lead.

Figure 7A:
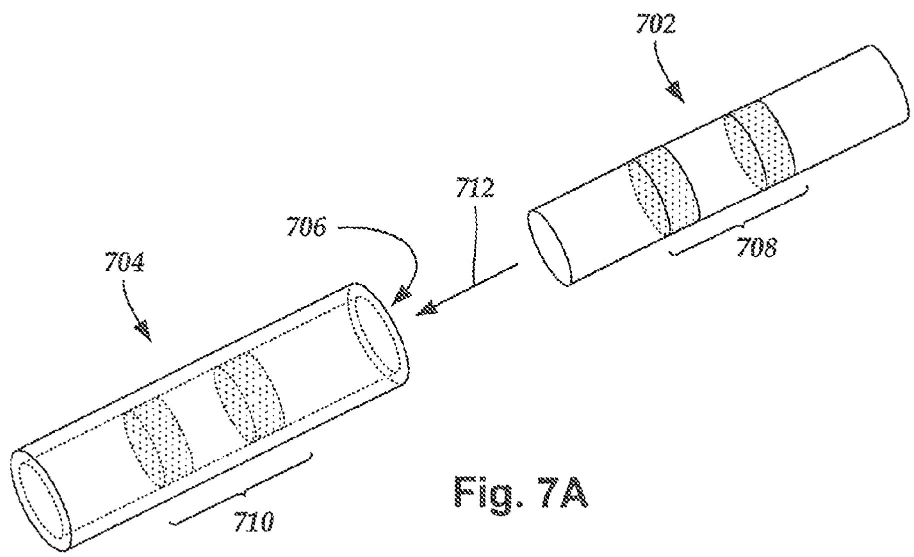
FIG. 7A is a schematic perspective view of one embodiment of a portion of a proximal end of a lead with a round cross-sectional shape and a portion of a connector with a port with a compatible cross-sectional shape, according to the invention.

In at least some embodiments, a connector can be configured and arranged to receive proximal ends of leads with different cross-sectional shapes. In a preferred embodiment, a port of a connector has a cross-sectional shape that matches, or nearly matches, the cross-sectional shape of a proximal end of a lead to facilitate insertion of the lead into the connector. FIG. 7A is a schematic perspective view of one embodiment of a portion of a proximal end of a lead 702 with a round cross-sectional shape and a portion of a connector 704 having a port 706 with a similar round cross-sectional shape. The lead 702 includes a plurality of terminals 708 that can align (and electrically couple) with a plurality of connector contacts 710 disposed in the port 706 when the lead 702 is inserted into the connector 704, as shown by directional arrow 712 (and as discussed above, with reference to FIGS. 4-6).

Figure 7B:
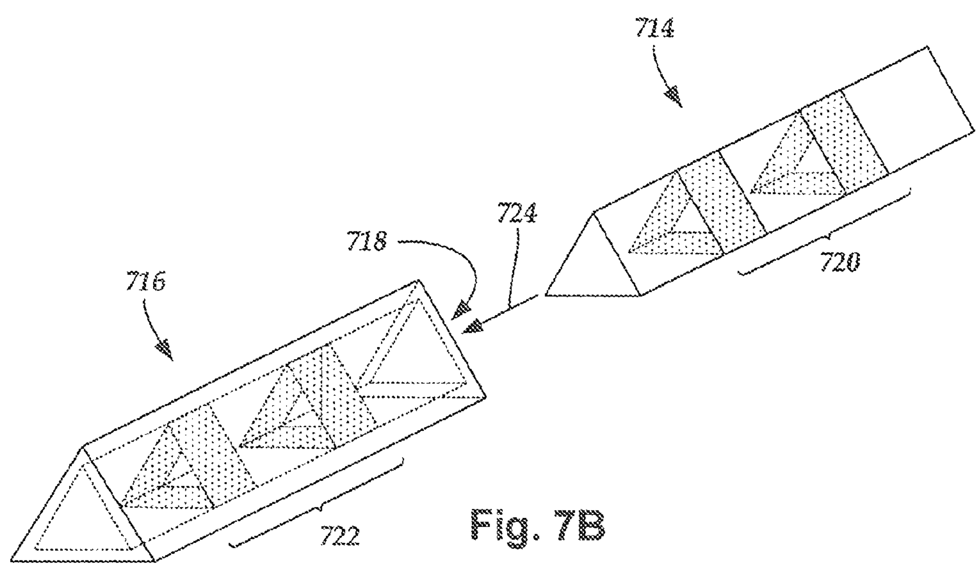
FIG. 7B is a schematic perspective view of one embodiment of a portion of a proximal end of a lead with a triangular cross-sectional shape and a portion of a connector with a port with a compatible cross-sectional shape, according to the invention.

In other embodiments, a proximal end of a lead has a cross-sectional shape that is not round. FIG. 7B is a schematic perspective view of one embodiment of a portion of a proximal end of a lead 714 with a triangular cross-sectional shape and a portion of a connector 716 having a port 718 with a similar triangular cross-sectional shape. The lead 714 includes a plurality of terminals 720 that can align (and electrically couple) with a plurality of connector contacts 722 disposed in the port 718 when the lead 714 is inserted into the connector 716, as shown by directional arrow 724 (and as discussed above, with reference to FIGS. 4-6). In at least some embodiments, a plurality of terminals are disposed around a lateral circumference of the lead 714.

Figure 7C:
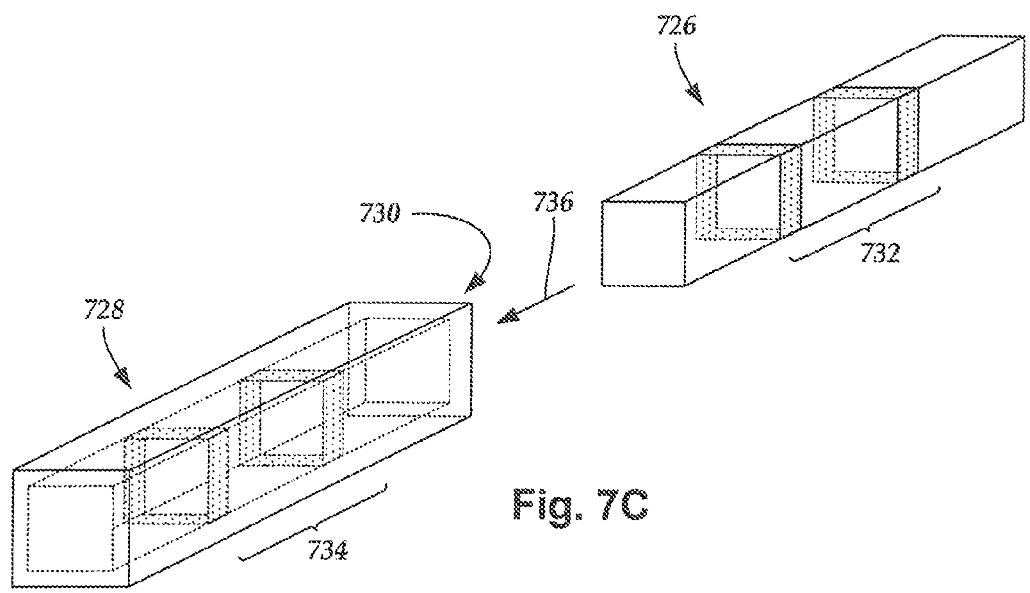
FIG. 7C is a schematic perspective view of one embodiment of a portion of a proximal end of a lead with a square cross-sectional shape and a portion of a connector with a port with a compatible cross-sectional shape, according to the invention.

FIG. 7C is a schematic perspective view of one embodiment of a portion of a proximal end of a lead 726 with a square cross-sectional shape and a portion of a connector 728 having a port 730 with a similar square cross-sectional shape. The lead 726 includes a plurality of terminals 732 that can align (and electrically couple) with a plurality of connector contacts 734 disposed in the port 730 when the lead 726 is inserted into the connector 728, as shown by directional arrow 736 (and as discussed above, with reference to FIGS. 4-6). In at least some embodiments, a plurality of terminals are disposed around a lateral circumference of the lead 726.

Figure 7D:
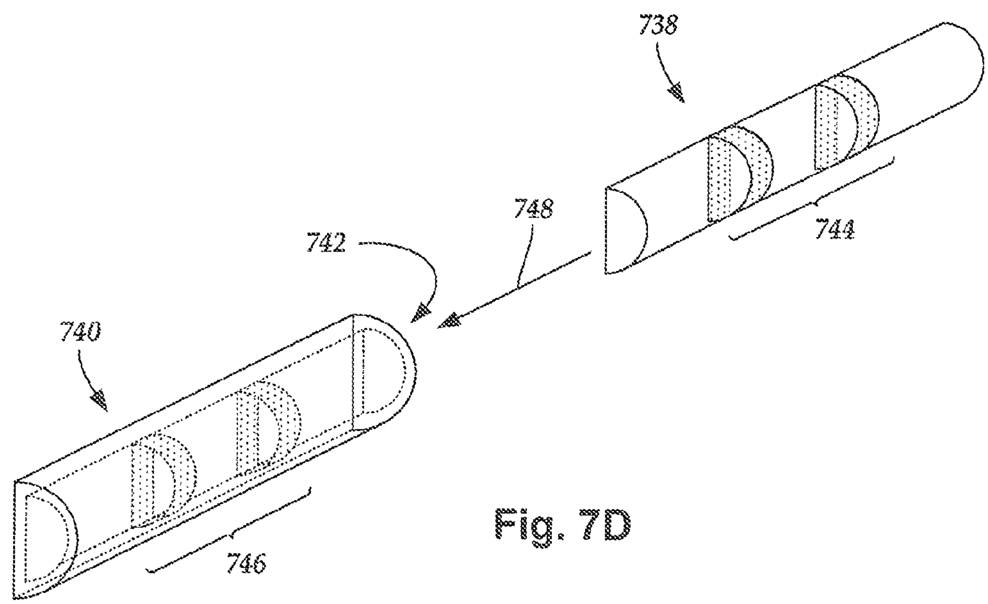
FIG. 7D is a schematic perspective view of one embodiment of a portion of a proximal end of a lead with a semi-circular cross-sectional shape and a portion of a connector with a port with a compatible cross-sectional shape, according to the invention.

FIG. 7D is a schematic perspective view of one embodiment of a portion of a proximal end of a lead 738 with a semi-circular cross-sectional shape and a portion of a connector 740 having a port 742 with a similar semi-circular cross-sectional shape. The lead 738 includes a plurality of terminals 744 that can align (and electrically couple) with a plurality of connector contacts 746 disposed in the port 742 when the lead 738 is inserted into the connector 740, as shown by directional arrow 748 (and as discussed above, with reference to FIGS. 4-6). In at least some embodiments, a plurality of terminals are disposed around a lateral circumference of the lead 738.

Proximal ends of leads may also have many other cross-sectional shapes, both regular or irregular. For example, proximal ends of leads may have cross-sectional shapes that are rectangular-shaped, oval-shaped, cross-shaped, diamond-shaped, and the like. It will be understood that proximal ends of leads may have other cross-sectional shapes as well. Additionally, ports of connectors may also have other cross-sectional shapes that match, or nearly match, the cross-sectional shapes of proximal ends of leads. Accordingly, ports of connectors may also have cross-sectional shapes that are rectangular-shaped, oval-shaped, cross-shaped, diamond-shaped, and the like. It will be understood that ports of connectors may have other cross-sectional shapes as well.

As discussed above, it may be advantageous to have a proximal end of a lead that has a cross-sectional shape that is different from the distal end of the lead. For example, it may be advantageous to provide a lead with a distal end having a round cross-sectional shape and a proximal end having a square cross-sectional shape. A lead having a distal end that is a different shape from a proximal end may facilitate with distinguishing between the two ends of the lead when, for example, both ends of the lead are obscured from view by tissue during a surgical procedure. Additionally, it may be an advantage to provide a lead with one or more non-circular proximal ends to dispose multiple terminals around a lateral circumference of the proximal end of the lead in order to increase terminal density without increasing the length of the connector that houses the terminals. It may also be an advantage to provide a lead with one or more non-circular proximal ends so that the proximal end of the lead can only be inserted into a connector in one or more particular orientations.

Figure 8:
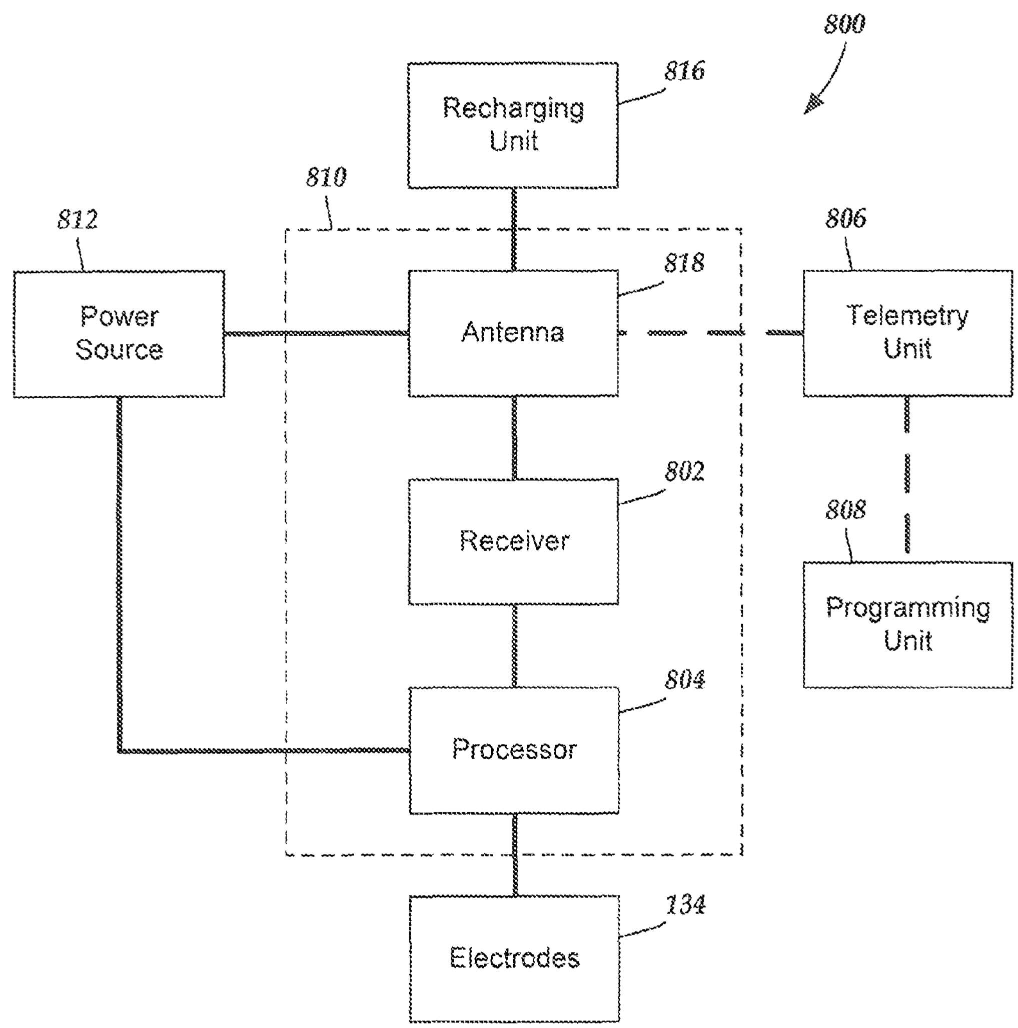
FIG. 8 is a schematic overview of one embodiment of components of a stimulation system, including an electronic subassembly disposed within a control module, according to the invention.

FIG. 8 is a schematic overview of one embodiment of components of an electrical stimulation system 800 including an electronic subassembly 810 disposed within a control module. It will be understood that the electrical stimulation system can include more, fewer, or different components and can have a variety of different configurations including those configurations disclosed in the stimulator references cited herein.

Some of the components (for example, power source 812, antenna 818, receiver 802, and processor 804) of the electrical stimulation system can be positioned on one or more circuit boards or similar carriers within a sealed housing of an implantable pulse generator, if desired. Any power source 812 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Patent Application Publication No. 2004/0059392, incorporated herein by reference.

As another alternative, power can be supplied by an external power source through inductive coupling via the optional antenna 818 or a secondary antenna. The external power source can be in a device that is mounted on the skin of the user or in a unit that is provided near the user on a permanent or periodic basis.

If the power source 812 is a rechargeable battery, the battery may be recharged using the optional antenna 818, if desired. Power can be provided to the battery for recharging by inductively coupling the battery through the antenna to a recharging unit 816 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. A processor 804 is generally included to control the timing and electrical characteristics of the electrical stimulation system. For example, the processor 804 can, if desired, control one or more of the timing, frequency, amplitude, duration, and waveform of the pulses. In addition, the processor 804 can select which electrodes can be used to provide stimulation, if desired. In some embodiments, the processor 804 may select which electrode(s) are cathodes and which electrode(s) are anodes. In some embodiments, the processor 804 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 808 that, for example, allows modification of pulse characteristics. In the illustrated embodiment, the processor 804 is coupled to a receiver 802 which, in turn, is coupled to the optional antenna 818. This allows the processor 804 to receive instructions from an external source to, for example, direct the pulse characteristics and the selection of electrodes, if desired.

In one embodiment, the antenna 818 is capable of receiving signals (e.g., RF signals) from an external telemetry unit 806 which is programmed by a programming unit 808. The programming unit 808 can be external to, or part of, the telemetry unit 806. The telemetry unit 806 can be a device that is worn on the skin of the user or can be carried by the user and can have a form similar to a pager, cellular phone, or remote control, if desired. As another alternative, the telemetry unit 806 may not be worn or carried by the user but may only be available at a home station or at a clinician's office. The programming unit 808 can be any unit that can provide information to the telemetry unit 806 for transmission to the electrical stimulation system 800. The programming unit 808 can be part of the telemetry unit 806 or can provide signals or information to the telemetry unit 806 via a wireless or wired connection. One example of a suitable programming unit is a computer operated by the user or clinician to send signals to the telemetry unit 806.

The signals sent to the processor 804 via the antenna 818 and receiver 802 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 800 to cease operation, to start operation, to start charging the battery, or to stop charging the battery. In other embodiments, the stimulation system does not include an antenna 818 or receiver 802 and the processor 804 operates as programmed.

Optionally, the electrical stimulation system 800 may include a transmitter (not shown) coupled to the processor 804 and the antenna 818 for transmitting signals back to the telemetry unit 806 or another unit capable of receiving the signals. For example, the electrical stimulation system 800 may transmit signals indicating whether the electrical stimulation system 800 is operating properly or not or indicating when the battery needs to be charged or the level of charge remaining in the battery. The processor 804 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed and desired to be protected by Letters Patent of the United States is:

1. A lead-connection system comprising:

a lead with a distal end and a proximal end, the lead comprising a plurality of electrodes disposed at the distal end, a plurality of terminals disposed at the proximal end, and a plurality of conductor wires disposed along the lead to electrically couple each of the plurality of electrodes to a different one of the plurality of terminals; and a connector configured and arranged for receiving a portion of the lead, the connector comprising a port configured and arranged for receiving the proximal end of the lead, and a plurality of connector contacts disposed in the port, wherein the plurality of connector contacts are divided into a plurality of sets of connector contacts with each set of connector contacts comprising at least two adjacent connector contacts of the plurality of connector contacts and each of the connector contacts belonging to only one of the sets, wherein, when the connector receives the proximal end of the lead, each set of connector contacts is configured and arranged to electrically couple with only one terminal of the plurality of terminals.

2. The lead-connection system of claim 1, wherein each set of connector contacts comprises the same number of connector contacts.

3. The lead-connection system of claim 1, wherein when the connector receives the proximal end of the lead a single connector contact of each set of connector contacts is configured and arranged to electrically couple with only one terminal of the plurality of terminals.

4. The lead-connection system of claim 1, wherein when the connector receives the proximal end of the lead a plurality of connector contacts of each set of connector contacts is configured and arranged to electrically couple with only one terminal of the plurality of terminals.

5. The lead-connection system of claim 1, wherein adjacent connector contacts of each set of connector contacts are separated from one another by an intra-set distance and each adjacent set of connector contacts are separated from one another by an inter-set distance.

6. The lead-connection system of claim 5, wherein either of the inter-set distance or the intra-set distance is greater than the other of the inter-set distance or the intra-set distance.

7. The lead-connection system of claim 1, further comprising at least one switch disposed on a housing of the connector, the at least one switch configured and arranged for controlling the activation of at least one connector contact of the plurality of connector contacts.

8. The lead-connection system of claim 7, wherein the at least one switch is configured and arranged for controlling the activation of at least one connector contact of each set of connector contacts.

9. The lead-connection system of claim 7, wherein the at least one switches is configured and arranged to de-activate at least one connector contact of the plurality of connector contacts.

10. The lead-connection system of claim 9, wherein the at least one switch is configured and arranged to de-activate at least one connector contact of each set of connector contacts.

11. The lead-connection system of claim 1, further including a processor in electrical communication with each connector contact of the plurality of connector contacts, the processor configured and arranged for controlling the amount of current passing through each connector contact when multiple connector contacts electrically couple with one of the plurality of terminals.

12. The lead-connection system of claim 1, wherein two or more of the plurality of terminals are disposed around a lateral circumference of the proximal end of the lead.

13. The lead-connection system of claim 1, wherein the distal end of the lead has a first cross-sectional shape and the proximal end of the lead has a second cross-sectional shape that is different from the first cross-sectional shape.

14. The lead-connection system of claim 13, wherein the proximal end of the lead has a cross-sectional shape that is one of rectangular, semi-circular, or oval-shaped.

15. An electrical stimulating system comprising:

a lead having a distal end and a proximal end, the lead comprising a plurality of electrodes disposed at the distal end, a plurality of terminals disposed at the proximal end, and a plurality of conductor wires coupling the plurality of electrodes electrically to the plurality of terminals;

a control module configured and arranged to electrically couple to the lead, the control module comprising a housing, and an electronic subassembly disposed in the housing; and a connector configured and arranged for receiving a portion of the lead, the connector comprising a port configured and arranged for receiving the proximal end of the lead, and a plurality of connector contacts disposed in the port, wherein the plurality of connector contacts are divided into a plurality of sets of connector contacts with each set of connector contacts comprising at least two adjacent connector contacts of the plurality of connector contacts and each of the connector contacts belonging to only one of the sets, wherein when the connector receives the proximal end of the lead each set of connector contacts is configured and arranged to electrically couple with only one terminal of the plurality of terminals.

16. The electrical stimulating system of claim 15, further including a lead extension having a distal end and at least one proximal end, the connector disposed on the distal end of the lead extension.

17. The electrical stimulating system of claim 16, wherein at least one of the at least one proximal ends is configured and arranged for insertion into another connector.

18. The electrical stimulating system of claim 15, wherein the connector is disposed on the control module.

19. A method for stimulating patient tissue, the method comprising:

implanting a lead into a patient, the lead comprising a plurality of electrodes disposed on a distal end electrically coupled to a plurality of terminals disposed on a proximal end by a plurality of contact wires;

disposing the proximal end of the lead into a port of a connector, the connector comprising a plurality of connector contacts disposed in the port, wherein the plurality of connector contacts are divided into a plurality of sets of connector contacts with each set of connector contacts comprising at least two adjacent connector contacts of the plurality of connector contacts and each of the connector contacts belonging to only one of the sets, wherein when the connector receives the proximal end of the lead each set of connector contacts is configured and arranged to electrically couple with only one terminal of the plurality of terminals; and providing electrical signals from at least one control module electrically coupled to the connector, the electrical signals electrically stimulating patient tissue using at least one of the plurality of electrodes disposed on the lead.

20. The method of claim 19, wherein providing electrical signals from the at least one control module to electrically stimulate patient tissue comprises activating at least one switch configured and arranged for controlling the activation of at least one connector contact of the plurality of connector contacts.

* * * * *